US012796984B2

(12) United States Patent
Nguyen et al.

(10) Patent No.: US 12,796,984 B2

(45) Date of Patent: Nov. 17, 2026

(54) NON-INVASIVE URINARY OUTPUT MONITORING SYSTEM

(71) Applicant: C. R. Bard, Inc., Franklin Lakes, NJ (US)

(72) Inventors: Hoang D. Nguyen, Marietta, GA (US); Serena R. Agrawal, Salt Lake City, UT (US); Hersh Ramesh Patel, Atlanta, GA (US); Jeffrey Dobkins, Mill Valley, CA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1109 days.

(21) Appl. No.: 17/682,785

(22) Filed: Feb. 28, 2022

(65) Prior Publication Data

US 2022/0296140 A1 Sep. 22, 2022

Related U.S. Application Data

(60) Provisional application No. 63/154,549, filed on Feb. 26, 2021.

(51) Int. Cl.

*A61B 5/20* (2006.01)
*A61B 5/00* (2006.01)
*A61B 10/00* (2006.01)

(52) U.S. Cl.

CPC ............ *A61B 5/208* (2013.01); *A61B 5/0002* (2013.01); *A61B 10/007* (2013.01); *A61B 2562/227* (2013.01)

(58) Field of Classification Search

CPC ..... A61B 5/208; A61B 5/0002; A61B 10/007; A61B 2562/227; A61B 5/0022;

(Continued)

(56) References Cited

U.S. PATENT DOCUMENTS 3,661,143 A 5/1972 Henkin
3,781,920 A 1/1974 Browne et al.

(Continued)

FOREIGN PATENT DOCUMENTS

CA 2882654 A1 10/2007
CN 2445749 Y 9/2001

(Continued)

OTHER PUBLICATIONS

Bard Medical, Criticore Disposables—Non I.C., 3 pages, www.bardmedical.com/products/patienl-moniloring-,ystems/criticore®-system/criticore®-disposables-non-ic/ Jan. 30, 2015.

(Continued)

*Primary Examiner* — Jennifer Robertson
*Assistant Examiner* — Elina Sohyun Jang
(74) *Attorney, Agent, or Firm* — Rutan & Tucker LLP

(57) ABSTRACT

Disclosed herein is a urinary output monitoring system configured to measure urinary flow or collect and measure a volume of fluid having a receptacle having a receptacle body including a plurality of volume markings, the receptacle configured to receive or hold a volume of fluid. The receptacle body includes a proximal portion including two lateral flaps and one front rigid flap, each of the flaps extending from the proximal portion, the two lateral flaps and the front rigid flap configured to secure the receptacle to a sanitary hardware device and prevent unwanted movement when engaged by a user, and a distal portion including an opening and a mating portion extending from the distal portion, the mating portion configured to detachably couple an attachment.

17 Claims, 8 Drawing Sheets

(58) Field of Classification Search

CPC ..... A61B 5/6891; A61B 10/0038; A61B 5/42; A61B 5/202; A61B 5/0059; A61B 5/1123; A61B 5/7275; A61B 5/0075; A61B 2217/005; A61B 2560/0266; A61B 2562/0252; A61B 2562/0257; G01F 1/661; E03D 11/02; E03D 9/00; G01N 21/31; G01N 21/3577; G01N 33/493; G01N 2021/3595; G01N 2201/061

See application file for complete search history.

(56) References Cited

U.S. PATENT DOCUMENTS 3,851,650 A 12/1974 Darling
3,919,455 A 11/1975 Sigdell et al.
4,276,889 A 7/1981 Kuntz et al.
4,286,590 A 9/1981 Murase
4,291,692 A 9/1981 Bowman et al.
4,296,749 A 10/1981 Pontifex
4,305,405 A 12/1981 Meisch
4,312,352 A 1/1982 Meisch et al.
4,343,316 A 8/1982 Jespersen
4,443,219 A 4/1984 Meisch et al.
4,448,207 A 5/1984 Parrish
4,509,366 A 4/1985 Matsushita et al.
4,532,936 A 8/1985 LeVeen et al.
4,658,834 A 4/1987 Blankenship et al.
4,712,567 A 12/1987 Gille et al.
4,723,950 A 2/1988 Lee
4,763,739 A 8/1988 Kasinoff
4,834,706 A 5/1989 Beck et al.
4,850,375 A 7/1989 Rosenberg
4,889,532 A 12/1989 Metz et al.
5,002,541 A 3/1991 Conkling et al.
5,146,637 A 9/1992 Bressler et al.
5,188,327 A 2/1993 White
5,409,014 A 4/1995 Napoli et al.
5,586,085 A 12/1996 Lichte
5,725,515 A 3/1998 Propp
5,733,319 A 3/1998 Neilson et al.
5,738,656 A 4/1998 Wagner
5,747,824 A 5/1998 Jung et al.
5,769,087 A 6/1998 Westphal et al.
5,807,278 A 9/1998 McRae
5,823,972 A 10/1998 McRae
5,891,051 A 4/1999 Han et al.
5,911,786 A 6/1999 Nielsen et al.
6,129,684 A 10/2000 Sippel et al.
6,132,407 A 10/2000 Genese et al.
6,250,152 B1 6/2001 Klein et al.
6,256,532 B1 7/2001 Cha
6,261,254 B1 7/2001 Baron et al.
6,434,418 B1 8/2002 Neal et al.
6,454,372 B1 9/2002 Yang
6,579,247 B1 6/2003 Abramovitch et al.
6,592,612 B1 7/2003 Samson et al.
6,709,420 B1 3/2004 Lincoln et al.
6,716,200 B2 4/2004 Bracken et al.
7,011,634 B2 3/2006 Paasch et al.
7,161,484 B2 1/2007 Tsoukalis
7,211,037 B2 5/2007 Briggs et al.
7,437,945 B1 10/2008 Feller
7,442,754 B2 10/2008 Tepper et al.
7,722,584 B2 5/2010 Tanaka et al.
7,739,907 B2 6/2010 Boiarski
7,871,385 B2 1/2011 Levinson
7,931,630 B2 4/2011 Nishtala et al.
7,976,533 B2 7/2011 Larsson
7,998,126 B1 8/2011 Fernandez
8,295,933 B2 10/2012 Gerber et al.
8,328,733 B2 12/2012 Forte et al.
8,328,734 B2 12/2012 Salvadori et al.
8,337,476 B2 12/2012 Greenwald et al.
8,374,688 B2 2/2013 Libbus et al.
8,403,884 B2 3/2013 Nishtala
8,471,231 B2 6/2013 Paz
8,663,128 B2 3/2014 Paz et al.
8,773,259 B2 7/2014 Judy et al.
8,790,277 B2 7/2014 Elliott et al.
8,790,320 B2 7/2014 Christensen
8,790,577 B2 7/2014 Mizumoto et al.
8,813,551 B2 8/2014 Boiarski
8,827,924 B2 9/2014 Paz et al.
8,832,558 B2 9/2014 Cardarelli et al.
8,900,196 B2 12/2014 Andino
9,045,887 B2 6/2015 O'Malley
9,050,046 B2 6/2015 Elliott et al.
9,074,920 B2 7/2015 Mendels et al.
9,216,242 B2 12/2015 Nishtala et al.
9,480,821 B2 11/2016 Ciccone et al.
9,592,034 B2 3/2017 Hall et al.
9,642,987 B2 5/2017 Bierman et al.
9,731,097 B2 8/2017 Andino et al.
9,895,095 B2 2/2018 Chen
9,928,341 B2 3/2018 Angelides
9,962,516 B2 5/2018 Lampotang et al.
10,071,202 B2 9/2018 Handler
10,182,747 B2 1/2019 Charlez et al.
10,245,008 B2 4/2019 Paige
10,301,807 B1 * 5/2019 Kolesar .................. A47K 13/26
10,362,981 B2 7/2019 Paz et al.
10,383,606 B1 8/2019 McCord et al.
10,448,875 B2 10/2019 Holt et al.
10,722,679 B2 7/2020 Lampotang et al.
10,799,386 B1 10/2020 Harrison, Sr.
10,881,320 B2 1/2021 Duval et al.
10,881,778 B2 1/2021 Scarpaci et al.
11,291,577 B2 4/2022 Seres et al.
11,473,958 B2 10/2022 Holt et al.
11,540,760 B1 1/2023 Guillemette
11,654,042 B2 5/2023 Hughett, Sr.
11,703,365 B2 7/2023 Tourchak et al.
12,083,261 B2 9/2024 Justice et al.
12,109,353 B2 10/2024 Cheng et al.
12,364,423 B2 7/2025 Cheng et al.
12,408,853 B2 9/2025 Kriscovich et al.
2001/0056226 A1 12/2001 Zodnik et al.
2002/0013518 A1 1/2002 West et al.
2002/0016719 A1 2/2002 Nemeth et al.
2002/0161314 A1 10/2002 Sarajarvi
2002/0193760 A1 12/2002 Thompson
2003/0000303 A1 1/2003 Livingston et al.
2003/0140697 A1 7/2003 Van Ee
2003/0163183 A1 8/2003 Carson
2003/0163287 A1 8/2003 Vock et al.
2004/0267086 A1 12/2004 Anstadt et al.
2005/0020958 A1 1/2005 Paolini et al.
2005/0065583 A1 3/2005 Voorhees et al.
2005/0172712 A1 8/2005 Nyce
2005/0247121 A1 11/2005 Pelster
2006/0065713 A1 3/2006 Kingery
2006/0100743 A1 5/2006 Townsend et al.
2006/0253091 A1 11/2006 Vernon
2007/0010797 A1 1/2007 Nishtala et al.
2007/0078444 A1 4/2007 Larsson
2007/0106177 A1 5/2007 Hama
2007/0145137 A1 6/2007 Mrowiec
2007/0225668 A1 9/2007 Otto
2007/0252714 A1 11/2007 Rondoni et al.
2008/0027409 A1 1/2008 Rudko et al.
2008/0217391 A1 9/2008 Roof et al.
2008/0312550 A1 12/2008 Nishtala et al.
2008/0312556 A1 12/2008 Dijkman
2009/0056020 A1 3/2009 Caminade et al.
2009/0099629 A1 4/2009 Carson et al.
2009/0157430 A1 6/2009 Rule et al.
2009/0171169 A1 7/2009 Nagata
2009/0287170 A1 11/2009 Otto
2009/0315684 A1 12/2009 Sacco et al.
2010/0064426 A1 3/2010 Chikara Imamura
2010/0094204 A1 4/2010 Nishtala
2010/0122963 A1 5/2010 Costa et al.
2010/0130949 A1 5/2010 Garcia
2010/0137743 A1 6/2010 Nishtala et al.

(56) References Cited

U.S. PATENT DOCUMENTS

2010/0262047 A1 10/2010 Genis
2011/0113540 A1 5/2011 Plate et al.
2011/0120219 A1 5/2011 Barlesi et al.
2011/0178425 A1 7/2011 Nishtala et al.
2011/0224636 A1 9/2011 Keisic
2011/0230824 A1 9/2011 Salinas et al.
2011/0238042 A1 9/2011 Davis et al.
2011/0251572 A1 10/2011 Nishtala et al.
2011/0263952 A1 10/2011 Bergman et al.
2012/0029408 A1 2/2012 Beaudin
2012/0035496 A1 2/2012 Denison et al.
2012/0059286 A1 3/2012 Hastings et al.
2012/0078137 A1 3/2012 Mendels et al.
2012/0078235 A1 3/2012 Martin et al.
2012/0095304 A1 4/2012 Biondi
2012/0108917 A1 5/2012 Libbus et al.
2012/0109008 A1 5/2012 Charlez et al.
2012/0118650 A1 5/2012 Gill
2012/0123233 A1 5/2012 Cohen
2012/0127103 A1 5/2012 Qualey et al.
2012/0226196 A1 9/2012 DiMino et al.
2012/0234434 A1 9/2012 Woodruff et al.
2012/0302917 A1 11/2012 Fitzgerald et al.
2012/0323144 A1 12/2012 Coston et al.
2012/0323502 A1 12/2012 Tanoura et al.
2013/0066166 A1 3/2013 Burnett et al.
2013/0109927 A1 5/2013 Menzel
2013/0109928 A1 5/2013 Menzel
2013/0131610 A1 5/2013 Dewaele et al.
2013/0218106 A1 8/2013 Coston et al.
2013/0245498 A1 9/2013 Delaney et al.
2013/0256486 A1 10/2013 Taylor
2013/0267871 A1 10/2013 Delaney et al.
2014/0039348 A1 2/2014 Bullington et al.
2014/0155781 A1 6/2014 Bullington et al.
2014/0155782 A1 6/2014 Bullington et al.
2014/0159921 A1 6/2014 Qualey et al.
2014/0166691 A1 6/2014 Chen et al.
2014/0187666 A1 7/2014 Aizenberg et al.
2014/0207085 A1 7/2014 Brandt et al.
2014/0243635 A1 8/2014 Arefieg
2014/0335490 A1 11/2014 Baarman et al.
2015/0120321 A1 4/2015 David et al.
2015/0233749 A1 8/2015 Wang et al.
2015/0342576 A1 12/2015 Hall et al.
2015/0343173 A1 12/2015 Tobescu et al.
2015/0359522 A1 12/2015 Recht et al.
2015/0362351 A1 12/2015 Joshi et al.
2016/0051176 A1 2/2016 Ramos et al.
2016/0051177 A1 2/2016 Chen
2016/0183819 A1 6/2016 Burnett et al.
2016/0374874 A1 12/2016 Trepanier et al.
2017/0035342 A1 2/2017 Elia et al.
2017/0043089 A1 2/2017 Handler
2017/0100068 A1 4/2017 Kostov
2017/0113000 A1 4/2017 Tobescu et al.
2017/0136209 A1 5/2017 Burnett et al.
2017/0140103 A1 5/2017 Angelides
2017/0196478 A1 7/2017 Hunter
2017/0202698 A1 7/2017 Zani et al.
2017/0241978 A1 8/2017 Duval
2017/0249445 A1 8/2017 Devries et al.
2017/0290540 A1 10/2017 Franco
2017/0291012 A1 10/2017 Iglesias
2017/0307423 A1 10/2017 Pahwa et al.
2017/0322197 A1 11/2017 Hall et al.
2018/0015251 A1 1/2018 Lampotang et al.
2018/0110455 A1 4/2018 Chang et al.
2018/0110456 A1 4/2018 Cooper et al.
2018/0160961 A1 6/2018 Gopinathan et al.
2018/0214122 A1 8/2018 Ansell et al.
2018/0214297 A1 8/2018 Hughett et al.
2018/0245967 A1 8/2018 Parker et al.
2018/0280236 A1 10/2018 Ludin et al.
2018/0306661 A1 10/2018 Stacey
2018/0317891 A1 11/2018 Kim
2018/0344234 A1 12/2018 McKinney et al.
2018/0344295 A1* 12/2018 Leibman .............. A61B 10/007
2019/0006047 A1 1/2019 Gorek et al.
2019/0017535 A1 1/2019 Ormsbee et al.
2019/0046102 A1 2/2019 Kushnir et al.
2019/0069829 A1 3/2019 Bulut
2019/0069830 A1 3/2019 Holt et al.
2019/0126006 A1 5/2019 Rehm et al.
2019/0150821 A1 5/2019 Waters et al.
2019/0167144 A1 6/2019 Jung et al.
2019/0201596 A1 7/2019 Luxon et al.
2019/0218826 A1 7/2019 Allen et al.
2019/0223844 A1 7/2019 Aboagye et al.
2019/0231244 A1* 8/2019 Swan ..................... A61B 5/202
2019/0247236 A1 8/2019 Sides et al.
2019/0254582 A1 8/2019 Wei et al.
2019/0298317 A1 10/2019 Colgan et al.
2019/0321588 A1 10/2019 Burnett et al.
2019/0328945 A1 10/2019 Analytis et al.
2019/0343445 A1 11/2019 Burnett et al.
2019/0358387 A1 11/2019 Elbadry et al.
2019/0365308 A1 12/2019 Laing et al.
2019/0381223 A1 12/2019 Culbert et al.
2020/0022637 A1 1/2020 Kurzrock et al.
2020/0064172 A1 2/2020 Tabaczewski et al.
2020/0085378 A1 3/2020 Burnett et al.
2020/0121300 A1* 4/2020 Moore .................... B67C 11/00
2020/0187863 A1 6/2020 Tu et al.
2020/0268302 A1 8/2020 Oh
2020/0268303 A1 8/2020 Oliva
2020/0289749 A1 9/2020 Odashima et al.
2020/0405524 A1 12/2020 Gill
2021/0000361 A1 1/2021 Lark et al.
2021/0054610 A1 2/2021 Hall et al.
2021/0077007 A1 3/2021 Jouret et al.
2021/0098124 A1 4/2021 Crook et al.
2021/0100533 A1 4/2021 Seres et al.
2021/0113130 A1 4/2021 Tran
2021/0202084 A1 7/2021 Cronin et al.
2021/0298653 A1 9/2021 Woodard et al.
2021/0299353 A1 9/2021 Mannu et al.
2021/0361211 A1 11/2021 Teramoto et al.
2022/0018692 A1 1/2022 Tourchak et al.
2022/0026001 A1 1/2022 Cheng et al.
2022/0026261 A1 1/2022 Funnell et al.
2022/0079487 A1 3/2022 Horiguchi et al.
2022/0192564 A1 6/2022 Kriscovich et al.
2022/0192565 A1 6/2022 Cheng et al.
2022/0192566 A1 6/2022 Cheng et al.
2022/0193375 A1 6/2022 Rehm et al.
2022/0233120 A1 7/2022 Beuret et al.
2022/0296406 A1 9/2022 Keelen
2022/0330867 A1 10/2022 Conley et al.
2022/0386917 A1 12/2022 Mann et al.
2023/0000259 A1 1/2023 Taylor
2023/0019703 A1 1/2023 Behzad et al.
2023/0022547 A1 1/2023 Cho et al.
2023/0025333 A1 1/2023 Patel et al.
2023/0028966 A1 1/2023 Franano
2023/0035669 A1 2/2023 Raja et al.
2023/0040915 A1 2/2023 Compton et al.
2023/0058553 A1 2/2023 Fallows et al.
2023/0060232 A1 3/2023 Patel et al.
2023/0084476 A1 3/2023 Robichaud et al.
2023/0089041 A1 3/2023 Handler
2024/0042120 A1 2/2024 Cheng et al.
2024/0081708 A1 3/2024 Kelly et al.
2024/0108268 A1 4/2024 Woodard et al.
2024/0252783 A1 8/2024 Waitkus et al.
2024/0347162 A1 10/2024 Meese et al.
2024/0360938 A1 10/2024 Cheng et al.
2024/0424186 A1 12/2024 Justice et al.
2025/0090066 A1 3/2025 Tourchak
2025/0120636 A1 4/2025 Compton et al.
2025/0205456 A1 6/2025 Rehm et al.
2025/0339073 A1 11/2025 Cheng et al.

(56) References Cited

U.S. PATENT DOCUMENTS

| | | | |
|---|---|---|---|
| 2026/0000330 | A1 | 1/2026 | Kriscovich et al. |
| 2026/0033762 | A1 | 2/2026 | Fallows et al. |
| 2026/0183468 | A1 | 7/2026 | Cheng et al. |

FOREIGN PATENT DOCUMENTS

| | | | |
|---|---|---|---|
| CN | 200951235 | Y | 9/2007 |
| CN | 201492414 | U | 6/2010 |
| CN | 102647939 | A | 8/2012 |
| CN | 103054559 | B | 5/2015 |
| CN | 104921738 | A | 9/2015 |
| CN | 205306875 | U | 6/2016 |
| CN | 107952140 | A | 4/2018 |
| CN | 109498013 | A | 3/2019 |
| CN | 110859636 | A | 3/2020 |
| CN | 112426156 | A | 3/2021 |
| EP | 0342028 | A2 | 11/1989 |
| ES | 2760470 | T3 | 5/2020 |
| GB | 2437549 | A | 10/2007 |
| GB | 2576743 | A | 3/2020 |
| JP | S49-75171 | A | 7/1974 |
| JP | S54-147066 | A | 11/1979 |
| JP | S58-190719 | A | 11/1983 |
| JP | S60-219517 | A | 11/1985 |
| JP | H02-057240 | B2 | 12/1990 |
| JP | H08-271301 | A | 10/1996 |
| JP | H10-104041 | A | 4/1998 |
| JP | 2007-303982 | A | 11/2007 |
| JP | 2008-524618 | A | 7/2008 |
| JP | 2009-068959 | A | 4/2009 |
| JP | 2010-121950 | A | 6/2010 |
| JP | 2010-530978 | A | 9/2010 |
| JP | 2012-105947 | A | 6/2012 |
| JP | 2012-225790 | A | 11/2012 |
| JP | 2018108356 | A | 7/2018 |
| KR | 20070115495 | A | 12/2007 |
| NL | 2013740 | A | 8/2016 |
| RU | 2615727 | C2 | 4/2017 |
| WO | 1981003427 | A1 | 12/1981 |
| WO | 2004045410 | A1 | 6/2004 |
| WO | 2013013782 | A2 | 1/2013 |
| WO | 20130178742 | A1 | 12/2013 |
| WO | 2014/043650 | A2 | 3/2014 |
| WO | 2014105755 | A1 | 7/2014 |
| WO | 2014108690 | A1 | 7/2014 |
| WO | 2014/135856 | A1 | 9/2014 |
| WO | 2014/151068 | A2 | 9/2014 |
| WO | 2014145971 | A2 | 9/2014 |
| WO | 201511402 | A1 | 1/2015 |
| WO | 2015/105916 | A1 | 7/2015 |
| WO | 2015/127390 | A1 | 8/2015 |
| WO | 2015191125 | A1 | 12/2015 |
| WO | 2016177901 | A1 | 11/2016 |
| WO | 2017/023794 | A1 | 2/2017 |
| WO | 2018156624 | A1 | 8/2018 |
| WO | 2019066357 | A1 | 4/2019 |
| WO | 2019106675 | A1 | 6/2019 |
| WO | 2019/226697 | A1 | 11/2019 |
| WO | 2020033752 | A1 | 2/2020 |
| WO | 2020154370 | A1 | 7/2020 |
| WO | 2020251893 | A1 | 12/2020 |
| WO | 2022108589 | A1 | 5/2022 |
| WO | 2022182794 | A1 | 9/2022 |
| WO | 2023022895 | A1 | 2/2023 |
| WO | 2023027871 | A1 | 3/2023 |
| WO | 2023076067 | A1 | 5/2023 |

OTHER PUBLICATIONS

Bard Medical, Criticore Infection Control Disposables, 3 pages, www.bardmedical.com/patienl-moniloring-,ystems/criticore®-system/criticore®-infection-control-disposables/ Jan. 30, 2015.

Bard Medical, Criticore Monitor, 11 pages, www.bardmedical.com/products/patient-monitoring-systems/criticore®—monitor/ Jan. 30, 2015.

Bard Medical, Urine Meiers, 3 pages, www.bardmedical.com/producls/urological-drainage/urine-collection/urinemeters/Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

PCT/US2019/045787 filed Aug. 8, 2019 International Preliminary Report on Patentability dated Feb. 16, 2021.

PCT/US2019/045787 filed Aug. 8, 2019 International Search Report and Written Opinion dated Oct. 2, 2019.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

U.S. Appl. No. 17/054,493, filed Nov. 10, 2020 Non-Final Office Action dated Nov. 24, 2021.

PCT/US20/61367 filed Nov. 19, 2020 International Search Report and Written Opinion dated Feb. 22, 2021.

U.S. Appl. No. 17/262,080, filed Jan. 21, 2021 Non-Final Office Action dated Apr. 6, 2023.

U.S. Appl. No. 17/373,535, filed Jul. 12, 2021 Notice of Allowance dated Feb. 23, 2023.

U.S. Appl. No. 17/556,907, filed Dec. 20, 2021 Restriction Requirement dated May 12, 2023.

PCT/US2022/017574 filed Feb. 23, 2022 Internation Search Report and Written Opinion dated Jun. 8, 2022.

Schlebusch, T. et al., "Bladder volume estimation from electrical impedance tomography" Physiological Measurement Institute of Physics Publishing, Bristol, GB. vol. 35 No. 9 Aug. 20, 2014. (Aug. 20, 2014).

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

U.S. Appl. No. 15/748,107, filed Jan. 26, 2018 Notice of Allowance dated Dec. 12, 2022.

U.S. Appl. No. 17/054,493, filed Nov. 10, 2020 Non-Final Office Action dated Jan. 27, 2023.

U.S. Appl. No. 17/3026,821, filed May 3, 2021 Non-Final Office Action dated Jan. 10, 2023.

U.S. Appl. No. 17/373,535, filed Jul. 12, 2021 Non-Final Office Action dated Nov. 9, 2022.

EP 20962628.2 filed May 31, 2023 Extended European Search Report dated Apr. 20, 2024.

EP 23188337.2 filed May 21, 2019 Extended European Search Report dated Dec. 4, 2023.

PCT/US2019/033389 filed Nov. 26, 2020 Extended European Search Report dated Jun. 4, 2021.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

PCT/US2022/046920 filed Oct. 17, 2022 International Search Report and Written Opinion dated Feb. 20, 2023.

U.S. Appl. No. 17/054,493, filed Nov. 10, 2020 Notice of Allowance dated Jan. 4, 2024.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

(56) References Cited

OTHER PUBLICATIONS

U.S. Appl. No. 17/373,546, filed Jul. 12, 2021 Notice of Allowance dated May 29, 2024.
U.S. Appl. No. 17/556,907, filed Dec. 20, 2021 Notice of Allowance dated Dec. 6, 2023.
U.S. Appl. No. 17/556,931, filed Dec. 20, 2021 Non-Final Office Action dated Mar. 27, 2024.
U.S. Appl. No. 17/556,931, filed Dec. 20, 2021 Restriction Requirement dated Feb. 22, 2024.
"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/552,250, filed Dec. 15, 2021 Advisory Action dated May 8, 2025.
U.S. Appl. No. 17/552,250, filed Dec. 15, 2021 Final Office Action dated Feb. 11, 2025.
U.S. Appl. No. 17/552,250, filed Dec. 15, 2021 Notice of Allowance dated May 20, 2025.
U.S. Appl. No. 17/556,931, filed Dec. 20, 2021 Advisory Action dated Dec. 6, 2024.
U.S. Appl. No. 17/556,931, filed Dec. 20, 2021 Notice of Allowance dated Mar. 18, 2025.
U.S. Appl. No. 17/587,938, filed Jan. 28, 2022 Non-Final Office Action dated May 12, 2025.
U.S. Appl. No. 17/587,938, filed Jan. 28, 2022 Restriction Requirement dated Jan. 22, 2025.
U.S. Appl. No. 17/833,682, filed Jun. 6, 2022 Final Office Action dated May 12, 2025.
U.S. Appl. No. 17/833,682, filed Jun. 6, 2022 Non-Final Office Action dated Jan. 15, 2025.
U.S. Appl. No. 17/863,223, filed Jul. 12, 2022 Non-Final Office Action dated Apr. 2, 2025.
U.S. Appl. No. 17/863,923, filed Jul. 13, 2022 Restriction Requirement dated May 21, 2025.
U.S. Appl. No. 17/870,698, filed Jul. 21, 2022 Non-Final Office Action dated Apr. 9, 2025.
U.S. Appl. No. 17/870,698, filed Jul. 21, 2022 Restriction Requirement dated Feb. 12, 2025.
U.S. Appl. No. 17/873,834, filed Jul. 26, 2022 Non-Final Office Action dated May 19, 2025.
U.S. Appl. No. 17/879,658, filed Aug. 2, 2022 Final Office Action dated May 14, 2025.
U.S. Appl. No. 17/879,658, filed Aug. 2, 2022 Non-Final Office Action dated Dec. 30, 2024.
U.S. Appl. No. 17/883,507, filed Aug. 8, 2022 Restriction Requirement dated May 19, 2025.
U.S. Appl. No. 17/893,435, filed Aug. 23, 2022 Non-Final Office Action dated Jan. 17, 2025.
U.S. Appl. No. 18/278,167, filed Aug. 21, 2023 Non-Final Office Action dated Apr. 24, 2025.
DFree Personal—Consumer Product Brochure, 2019.
DFree Pro Brochure 2019.
Leonhäuser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary Volume Monitoring System Based on Bio-Impedance."—Engineering; vol. 5; pp. 321-325; 2013.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
SECA product catalog, https://us.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/373,546, filed Jul. 12, 2021 Non-Final Office Action dated Nov. 1, 2023.
"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).
U.S. Appl. No. 17/552,250, filed Dec. 15, 2021 Non-Final Office Action dated Sep. 19, 2024.
U.S. Appl. No. 17/556,931, filed Dec. 20, 2021 Final Office Action dated Oct. 1, 2024.
U.S. Appl. No. 17/560,079, filed Dec. 22, 2021 Notice of Allowance dated Oct. 29. 2024.
U.S. Appl. No. 17/833,682, filed Jun. 6, 2022 Advisory Action dated Mar. 24, 2026.
U.S. Appl. No. 17/833,682, filed Jun. 6, 2022 Final Office Action dated Jan. 16, 2026.
U.S. Appl. No. 17/863,923, filed Jul. 13, 2022 Notice of Allowance dated Feb. 27, 2026.
U.S. Appl. No. 17/873,834, filed Jul. 26, 2022 Advisory Action dated Jan. 30, 2026.
U.S. Appl. No. 17/873,834, filed Jul. 26, 2022 Non-Final Office Action dated Mar. 12, 2026.
U.S. Appl. No. 17/941,941, filed Sep. 9, 2022 Final Office Action dated Jan. 30, 2026.
U.S. Appl. No. 18/682,075, filed Feb. 7, 2024 Advisory Action dated Mar. 6, 2026.
U.S. Appl. No. 18/682,082, filed Feb. 7, 2024 Non-Final Office Action dated Feb. 11, 2026.
U.S. Appl. No. 18/701,916, filed Apr. 16, 2024 Non-Final Office Action dated Mar. 23, 2026.
Wilson NPL SWIR Imaging 101 https://~wilson.com/swir-imaging-101-what-can-it-do-for-you/ Jan. 2021 (Year: 2021).
U.S. Appl. No. 17/863,223, filed Jul. 12, 2022 Advisory Action dated Dec. 1, 2025.
U.S. Appl. No. 17/863,923, filed Jul. 13, 2022 Non-Final Office Action dated Oct. 22, 2025.
U.S. Appl. No. 17/870,698, filed Jul. 21, 2022 Non-Final Office Action dated Nov. 21, 2025.
U.S. Appl. No. 17/873,834, filed Jul. 26, 2022 Final Office Action dated Nov. 28, 2025.
U.S. Appl. No. 17/879,658, filed Aug. 2, 2022 Non-Final Office Action dated Nov. 18, 2025.
U.S. Appl. No. 18/036,335, filed May 10, 2023 Notice of Allowance dated Oct. 21, 2025.
U.S. Appl. No. 18/278,167, filed Aug. 21, 2023 Notice of Allowance dated Oct. 16, 2025.
U.S. Appl. No. 17/833,682, filed Jun. 6, 2022 Non-Final Office Action dated Sep. 15, 2025.
U.S. Appl. No. 17/863,223, filed Jul. 12, 2022 Final Office Action dated Sep. 24, 2025.
U.S. Appl. No. 17/870,698, filed Jul. 21, 2022 Final Office Action dated Jul. 29, 2025.
U.S. Appl. No. 17/883,507, filed Aug. 8, 2022 Non-Final Office Action dated Aug. 27, 2025.
U.S. Appl. No. 17/893,435, filed Aug. 23, 2022 Notice of Allowance dated Jul. 11, 2025.
U.S. Appl. No. 17/941,941, filed Sep. 9, 2022 Non-Final Office Action dated Aug. 22, 2025.
U.S. Appl. No. 17/941,941, filed Sep. 9, 2022 Restriction Requirement dated May 28, 2025.
U.S. Appl. No. 18/036,335, filed May 10, 2023 Non-Final Office Action dated Jun. 18, 2025.
U.S. Appl. No. 18/682,075, filed Feb. 7, 2024 Non-Final Office Action dated Jun. 18, 2025.
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).

(56) References Cited

OTHER PUBLICATIONS

Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).
U.S. Appl. No. 17/863,223, filed Jul. 12, 2022 Non-Final Office Action dated Apr. 21, 2026.
U.S. Appl. No. 17/870,698, filed Jul. 21, 2022 Final Office Action dated Jun. 17, 2026.
U.S. Appl. No. 17/879,658, filed Aug. 2, 2022 Final Office Action dated Apr. 24, 2026.
U.S. Appl. No. 17/883,507, filed Aug. 8, 2022 Notice of Allowance dated Jun. 8, 2025.
U.S. Appl. No. 17/941,941, filed Sep. 9, 2022 Non-Final Office Action dated Jun. 25, 2026.
U.S. Appl. No. 18/538,136 filed Dec. 13, 2023 Restriction Requirement dated May 14, 2026.
U.S. Appl. No. 18/682,082, filed Feb. 7, 2024 Final Office Action dated Jun. 11, 2026.
U.S. Appl. No. 18/765,516, filed Jul. 8, 2024 Non-Final Office Action dated May 21, 2026.

* cited by examiner

NON-INVASIVE URINARY OUTPUT MONITORING SYSTEM

PRIORITY

This application claims the benefit of priority to U.S. Provisional Application No. 63/154,549 filed Feb. 26, 2021, which is incorporated by reference in its entirety into this application.

BACKGROUND

Measuring urinary flow, measuring urinary volume and urine sample collection can be difficult for ambulatory patients. Many systems require patients to use two separate systems for urinary flow measurement and measuring urinary volume and urine sample collection. Furthermore, many urine hats rest on a toilet seat and can move when a patient sits on the toilet seat, leading to spillage, mess, loss of sample or the need to secure the urine hat to the seat. It would be beneficial to patients and clinicians to have one system that measured urinary flow, measured urinary volume, and allowed for urine sample collection. Disclosed herein is a system, apparatus and method that address the foregoing.

SUMMARY

Disclosed herein is a urinary output monitoring system configured to measure urinary flow or collect and measure a volume of fluid. The urinary output monitoring system includes a receptacle having a receptacle body configured to receive or hold a volume of fluid, the receptacle body having a plurality of volume markings. The receptacle body includes a proximal portion including two lateral flaps and one front rigid flap, each flap extending from the proximal portion and configured to secure the receptacle to a sanitary hardware device to prevent unwanted movement when engaged by a user, and a distal portion including an opening and a mating portion extending from the distal portion, the mating portion configured to detachably couple an attachment.

In some embodiments, the attachment includes a reusable flow meter or a cap.

In some embodiments, the flow meter includes a pinwheel flow meter having a proximal end including a proximal opening, the proximal end having a threaded portion configured to detachably couple to the mating portion, a distal opening, a lumen having a pinwheel within the lumen, the pinwheel having a magnet, and a Hall-effect sensor.

In some embodiments, the Hall-effect sensor is in wireless communication with a console, or wired to the console, the console including a processor, an energy source, and non-transitory computer-readable medium having stored thereon a plurality of logic modules.

In some embodiments, the plurality of logic modules, when executed by the processor, are configured to perform operations including activating the Hall-effect sensor, detecting and acquiring a plurality of pulses from the magnet over a unit of time, associating the plurality of pulses with a rate of flow value, associating the rate of flow value with a time of day value in a rate of flow value-time of day value pairing, storing the rate of flow-time of day value pairings, and transmitting the rate of flow-time of day pairings to a computing device.

In some embodiments, the console is in wireless communication with a computing device.

In some embodiments, the threaded portion of the pinwheel flow meter includes an external threaded portion or an internal threaded portion.

In some embodiments, the cap, when coupled with the mating portion, is configured seal a volume of fluid within the receptacle.

In some embodiments, the receptacle body includes an inverse truncated elliptical cone.

In some embodiments, each of the two lateral flaps include a score line configured to allow each flap to fold downward to couple with a sanitary hardware device.

In some embodiments, the sanitary hardware device includes a toilet.

In some embodiments, the mating portion of the receptacle body includes internal threads or external threads.

Also disclosed herein is a method of measuring urinary flow including coupling a flow meter to a mating portion of a receptacle, coupling the receptacle to a sanitary hardware device, acquiring a volume of fluid within the receptacle, and measuring the flow rate of the volume of fluid using the flow meter.

In some embodiments, coupling the flow meter to the mating portion of the receptacle includes the receptacle having a receptacle body having a proximal portion including two lateral flaps and one front rigid flap extending from the proximal portion, a distal portion having an opening and the mating portion extending therefrom, the mating portion having threads configured to detachably couple a reusable flow meter.

In some embodiments, coupling the flow meter to the mating portion of the receptacle includes detachably coupling a reusable pinwheel flow meter having a proximal end having a proximal opening, the proximal end having a threaded portion configured to couple to the mating portion, a distal opening, a lumen having a pinwheel, and a Hall-effect sensor in communication with a console including a processor, an energy source and non-transitory computer-readable medium having stored thereon a plurality of logic modules.

In some embodiments, coupling the flow meter to the mating portion of the receptacle includes detachably coupling the reusable flow meter to the mating portion with a press fit, a twist fit, a snap fit or an interference fit.

In some embodiments, coupling the receptacle to the sanitary hardware device includes folding each of the two lateral flaps downward along a score line to couple each lateral flap to a side of the sanitary hardware device, and coupling the front rigid flap to a front of the sanitary hardware device.

Also disclosed herein is a method of measuring and collecting urinary output including coupling a cap to a mating portion of a receptacle, coupling the receptacle to a sanitary hardware device, acquiring a volume of fluid within the receptacle, and measuring the volume of fluid within the receptacle using a plurality of volume markers.

In some embodiments, coupling the cap to the mating portion of the receptacle includes coupling the cap to the mating portion having threads thereon with a press fit, a twist fit, a snap fit or an interference fit.

In some embodiments, coupling the receptacle to the sanitary hardware device includes folding each of two lateral flaps and a rigid front flap downward along a score line to couple the receptacle to the sanitary hardware device.

In some embodiments, measuring the volume of fluid within the receptacle using the plurality of volume markers includes visually determining the volume of fluid using the plurality of volume markers.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
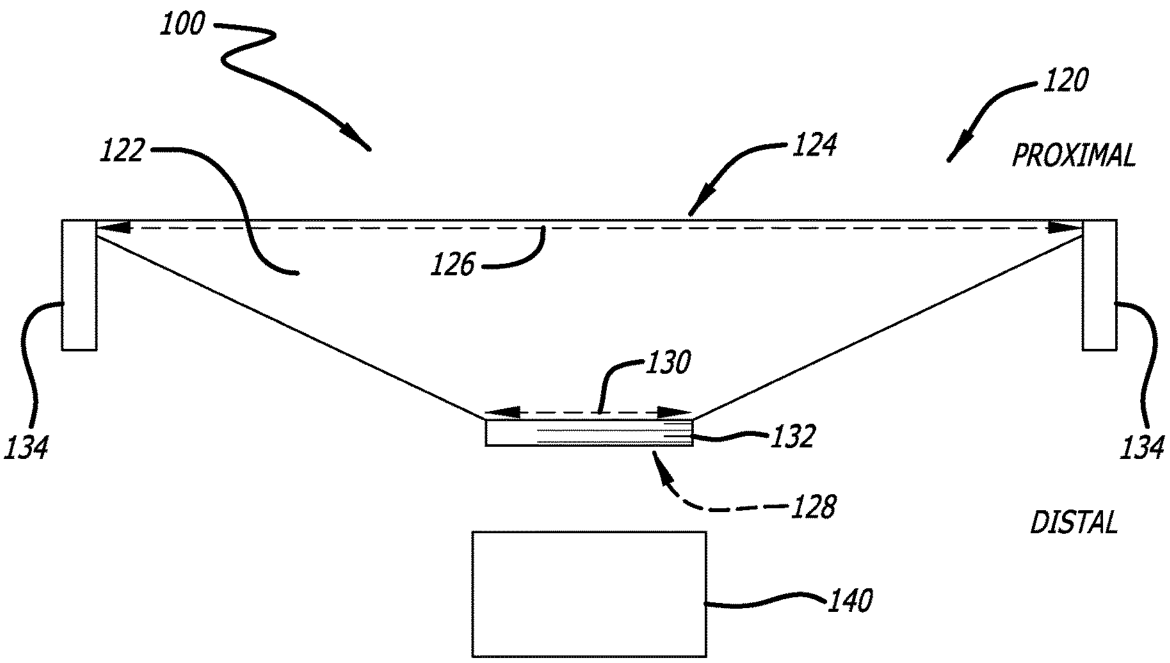
FIG. 1A illustrates a cross sectional front view of a non-invasive automated urine output monitoring system including a receptacle coupled to a flow meter, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical, or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

Unless defined otherwise, all technical and scientific terms used herein have the same meaning as commonly understood by those of ordinary skill in the art.

FIG. 1A illustrates a cross sectional front view of a non-invasive automated urine output monitoring system ("system") 100 including a receptacle 120 coupled to a flow meter 140, in accordance with some embodiments. In some embodiments, the system 100 includes the receptacle 120 configured to acquire and direct a volume of fluid through the flow meter 140 to measure and analyze the flow rate of the volume of fluid, in a mechanism that will be described in more detail herein. In some embodiments, the receptacle 120 includes a receptacle body 122 that may be shaped in an inverted cone, an inverted dome, or the like. The receptacle body 122 may have a proximal portion having a proximal opening 124 including a proximal width 126 and a distal portion having a distal width 130 and an opening 128. The receptacle 120 may be configured to direct the volume of fluid to the opening 128 with the proximal width 126 being greater than the distal width 130. The distal portion may include a mating portion 132 configured to couple various attachments thereon, including the flow meter 140 or a cap, that will be described in more detail herein. In some embodiments, a user may select which attachment to couple to the mating portion 132 to define the use of the receptacle 120. For example, if the user wants to measure urinary flow including urinary flow rate, the user could couple the flow meter 140 to the mating portion 132 of the receptacle 120. If the user wants to measure urinary output, the user may couple a cap to the mating portion 132 of the receptacle 120, as will be described herein. In some embodiments, the mating portion 132 may include one or more threads configured to couple the various attachments to the mating portion 132.

In some embodiments, the mating portion 132 may include one or more threads configured to couple the attachment to the mating portion 132. In some embodiments, the one or more threads may include external threads or internal threads. In some embodiments, the receptacle 120 is configured to couple to a sanitary hardware device, including a seat of the sanitary hardware device and be suspended from the seat of the sanitary hardware device. As used herein, the sanitary hardware device includes a toilet. The proximal portion of the receptacle body 122 includes a plurality of flaps extending therefrom including two or more lateral flaps 134. In some embodiments, the receptacle 120 may be 3D printed, extruded, injection molded, or the like.

Figure 1B:
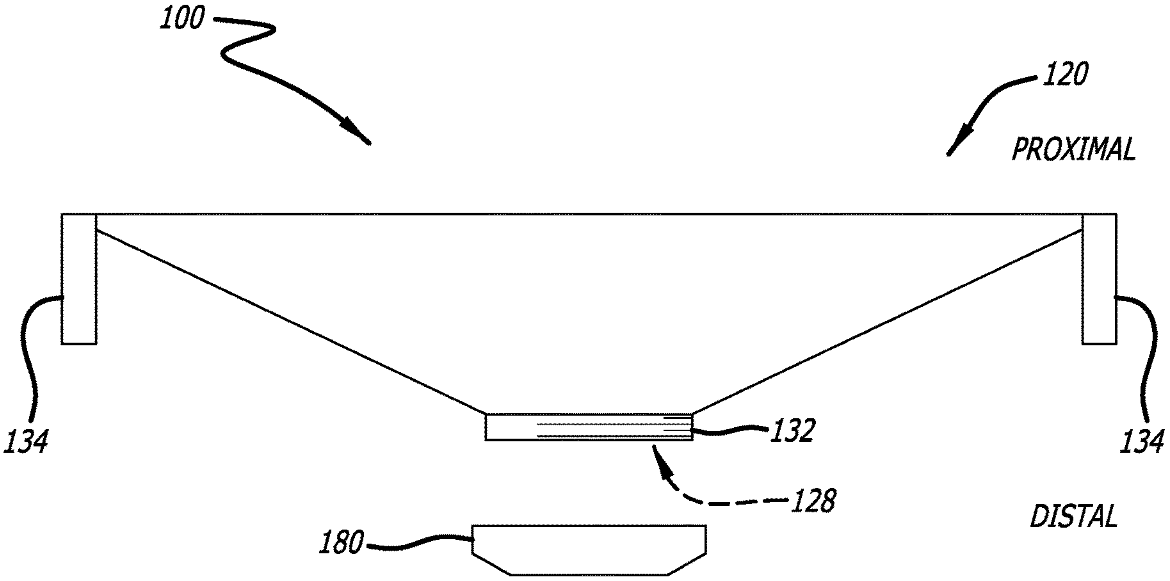
FIG. 1B illustrates a cross sectional front view of the non-invasive automated urine output monitoring system including the receptacle coupled to a cap, in accordance with some embodiments.

FIG. 1B illustrates a cross sectional front view of the non-invasive automated urine output monitoring system 100 including the receptacle 120 coupled to a cap 180, in accordance with some embodiments. In some embodiments, the receptacle 120 is as described above. The cap 180 may be configured to couple to the mating portion 132 of the receptacle 120. The cap 180 being coupled to the mating portion 132 allows the receptacle 120 to retain and measure the entirety of the volume of fluid received within the receptacle 120. A portion of or the entirety of the volume of fluid may be used for further analysis.

Figure 2:
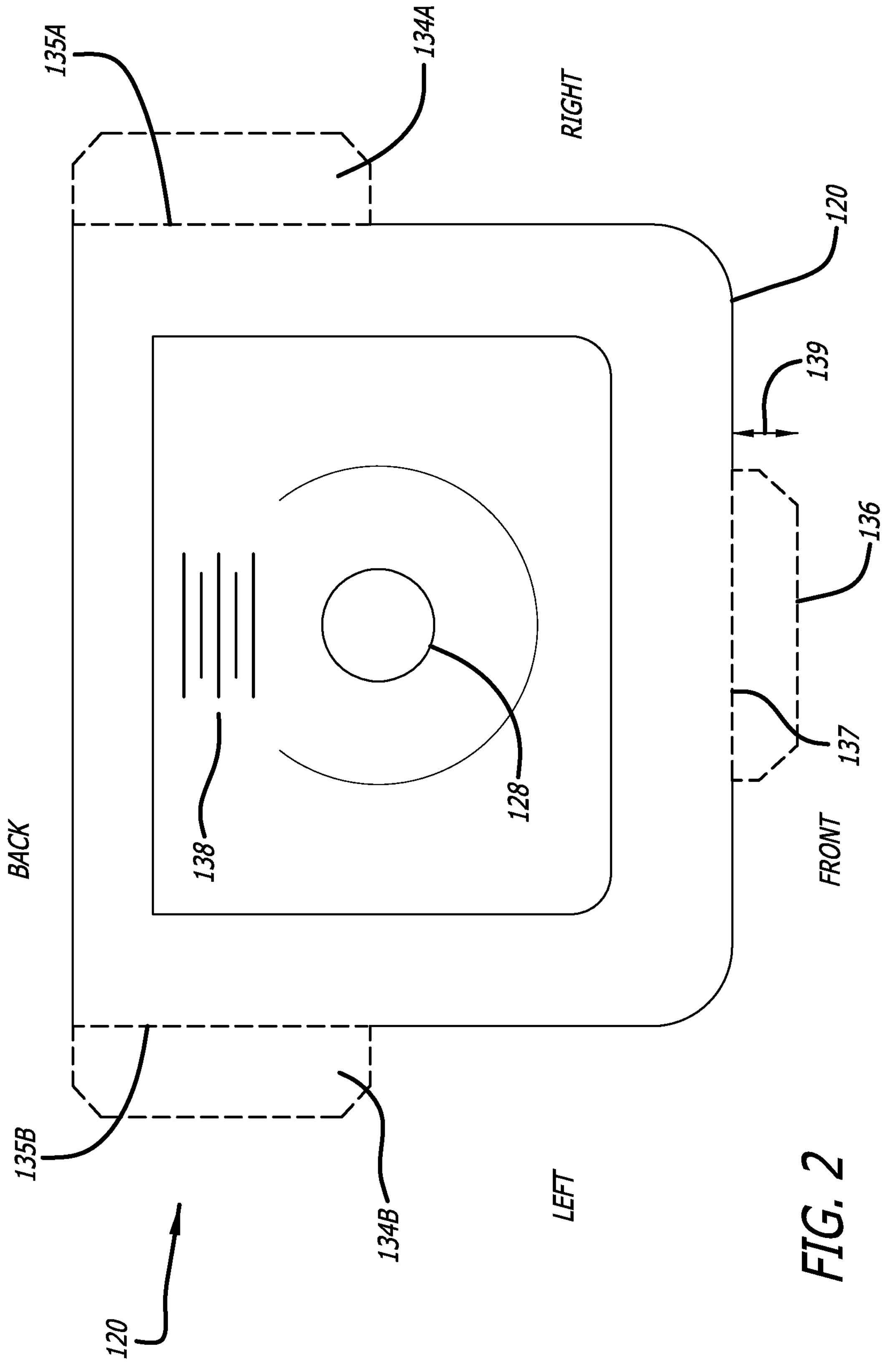
FIG. 2 illustrates a plan view of the receptacle, in accordance with some embodiments.

FIG. 2 illustrates a plan view of the receptacle 120, in accordance with some embodiments. The receptacle 120 includes the plurality of flaps 134A/134B and 136 extending from the proximal portion and configured to secure the receptacle 120 to the sanitary hardware device. In some embodiments, the plurality of flaps include the rigid front flap 136 configured secure the receptacle 120 to a front of the sanitary hardware device and may be configured to prevent unwanted movement backwards when a user engages the receptacle 120. In some embodiments, the rigid front flap 136 may include a rigid front flap depth 139 that is configured to provide the rigidity for the front flap 136. The proximal portion of the receptacle 120 includes the two or more lateral flaps 134A/134B. In some embodiments, the lateral flaps 134A/134B may be configured to bend downward, to couple the lateral flaps 134A/134B to the sanitary hardware device. As illustrated in FIG. 2, the receptacle 120 includes a left lateral flap 134B and a right lateral flap 134A. In some embodiments, the right lateral flap 134A and the left lateral flap 134B each include a score line 135A/135B, a thinned portion of each flap configured to allow each flap 134A/134B to be folded downward along the score line 135A/135B. In some embodiments, the rigid front flap 136 may already be folded downward or may include a front flap score line 137 configured to allow the user to fold the rigid front flap 136 downward before use. In some embodiments, the user may couple the receptacle 120 to the sanitary hardware device, then fold the left lateral flap 134B, the right lateral flap 134A and the rigid front flap 136 downward or the user may fold the left lateral flap 134B, the right lateral flap 134A and the rigid front flap 136 downward and then couple the receptacle 120 to the sanitary hardware device. In an embodiment, the right lateral flap 134A, the left lateral flap 134B and the rigid front flap 136 may be pre-folded.

In some embodiments, the receptacle 120 may include a plurality of volume markings 138 within the receptacle 120. The plurality of volume markings 138 may be used by the user to measure the volume of fluid collected within the receptacle 120. In some embodiments, the plurality of volume markings 138 may be located towards the back, the front, the left, the right or a combination thereof. The plurality of volume markings 138 may be measured in fluid ounces or milliliters. In some embodiments, the plurality of volume markings 138 may be etched, engraved, stenciled, printed or the like on the receptacle 120.

Figure 3A:
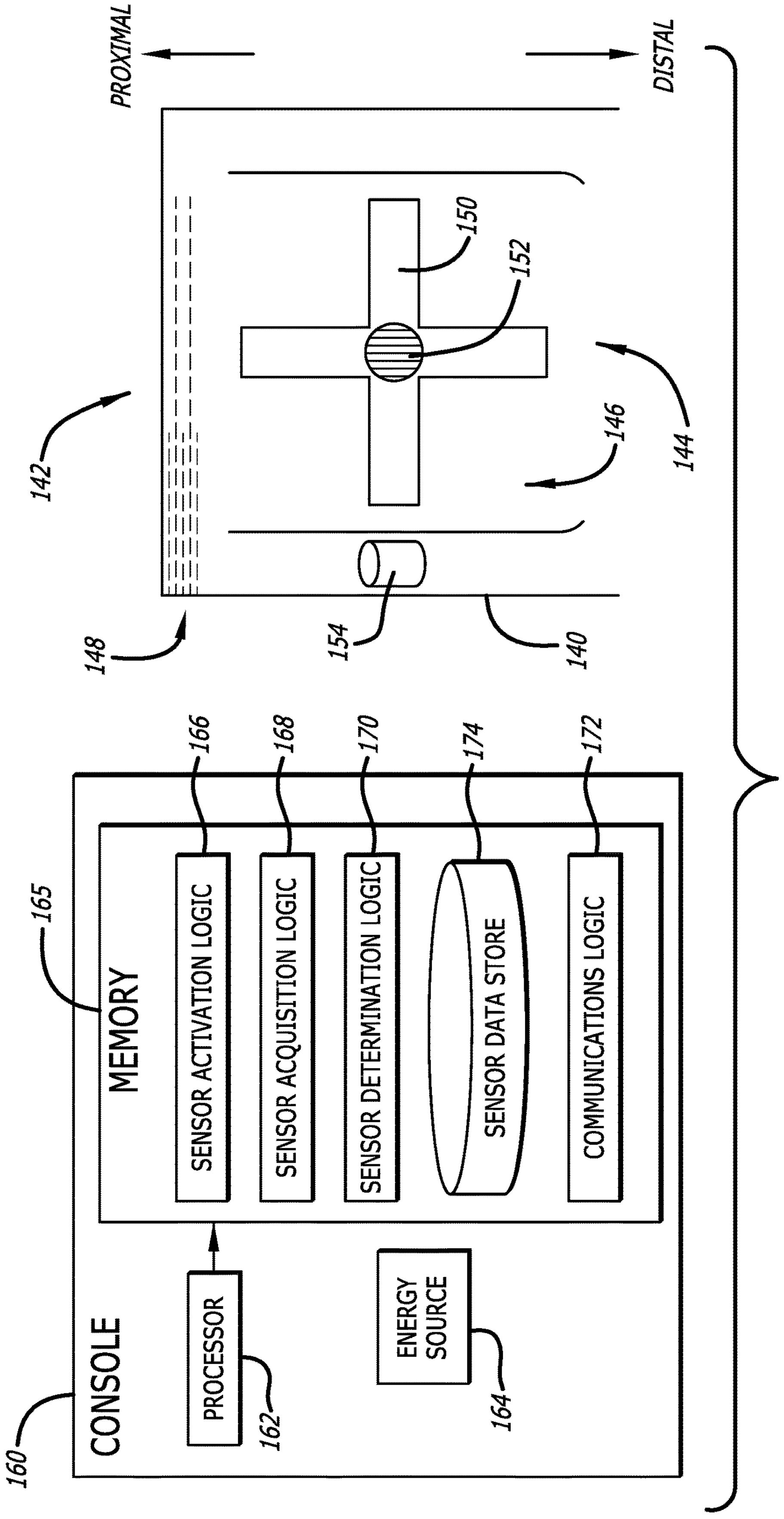
FIG. 3A illustrates a cross sectional view of the flow meter and a block diagram of various components off the non-invasive automated urine output monitoring system including a console, in accordance with some embodiments.

FIG. 3A illustrates a cross sectional view of the flow meter 140 and a block diagram of various components of the non-invasive automated urine output monitoring system 100 including a console 160, in accordance with some embodiments. In some embodiments, the flow meter 140 is reusable. The flow meter 140 includes a proximal end having a proximal opening 142, a distal end having a distal opening 144 and a lumen 146 therethrough. In some embodiments, the proximal end of the flow meter 140 includes a threaded portion 148 configured to couple the flow meter 140 with the mating portion 132 of the receptacle 120 (see FIG. 1A). In some embodiments, the threaded portion 148 may include external threads or internal threads. In some embodiments, the flow meter 140 may be configured to be coupled to the mating portion 132 of the receptacle 120 in a twist fit, snap fit, interference fit, screw fit, or the like. In an embodiments, the proximal end and the distal end of the flow meter 140 may be configured to include external threads thereon, to allow a user to couple the flow meter 140 to the mating portion 132 of the receptacle 120 in any orientation. In some embodiments, the flow meter 140 may include a pinwheel flow meter, an electromagnetic flow meter, a turbine flow meter, an ultrasonic flow meter, or the like. As used herein, the flow meter 140 refers to a pinwheel flow meter. In some embodiments, the flow meter 140 may be configured to have a pinwheel 150 configured to rotate annularly about a magnet 152 located in the middle of the pinwheel 150. The magnet 152 may be configured to generate a magnetic field that may be detected by a Hall-effect sensor 154. In some embodiments, the Hall-effect sensor 154 may be coupled to the outside of the flow meter 140, or as illustrated in FIG. 3A, may be located between the outside of the flow meter 140 and the lumen 146. The pinwheel 150 may be located within the lumen 146 and configured to rotate annularly by a volume of fluid flowing through the lumen 146. The rotating pinwheel 150 and the magnet 152 may be configured to trigger the Hall-effect sensor 154 in a mechanism that will be described in more detail herein.

The flow meter 140 may be wired to the console 160 or in wirelessly communication with the console 160. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like. In some embodiments, the console 160 may be located within the flow meter 140, coupled to the outside of the flow meter 140 or the like. In some embodiments, the console 160 includes one or more processors 162, one or more energy sources 164 configured to provide energy to the console 160 and to the Hall-effect sensor 154, and non-transitory computer-readable medium ("memory") 165 having a plurality of logic modules. In some embodiments, the plurality of logic modules may include one or more of: a sensor activation logic 166, a sensor acquisition logic 168, a sensor determination logic 170, a sensor data store 174, and a communications logic 172. In some embodiments, the Hall-effect sensor activation logic 166 may be configured to activate the Hall-effect sensor 154. In some embodiments, the Hall-effect sensor 154 may be activated whenever the flow meter 140 is coupled to the receptacle 120. In some embodiments, the Hall-effect sensor acquisition logic 168 may be configured to detect and acquire a plurality of pulses from the Hall-effect sensor 154 over a unit of time. In some embodiments, the Hall-effect determination logic 170 may be configured to determine the flow rate of the volume of fluid passing through the flow meter 140. In some embodiments, the Hall-effect determination logic 170 may associate the plurality of detected pulses with the unit of time the plurality of pulses were detected in a rate of flow value and associate the rate of flow value with a time of day value in a {rate of flow value, time of day value} pairing. The Hall-effect determination logic 170 may further convert the rate of flow value to a metric system value in liters/second. In some embodiments, the communications logic 172 may be configured to transmit the {rate of flow value, time of day value} pairing to a computing device, an electronic medical record, or the like. In some embodiments, the Hall-effect data store 174 may be configured to store the {rate of flow value, time of day} pairings.

Figure 3C:
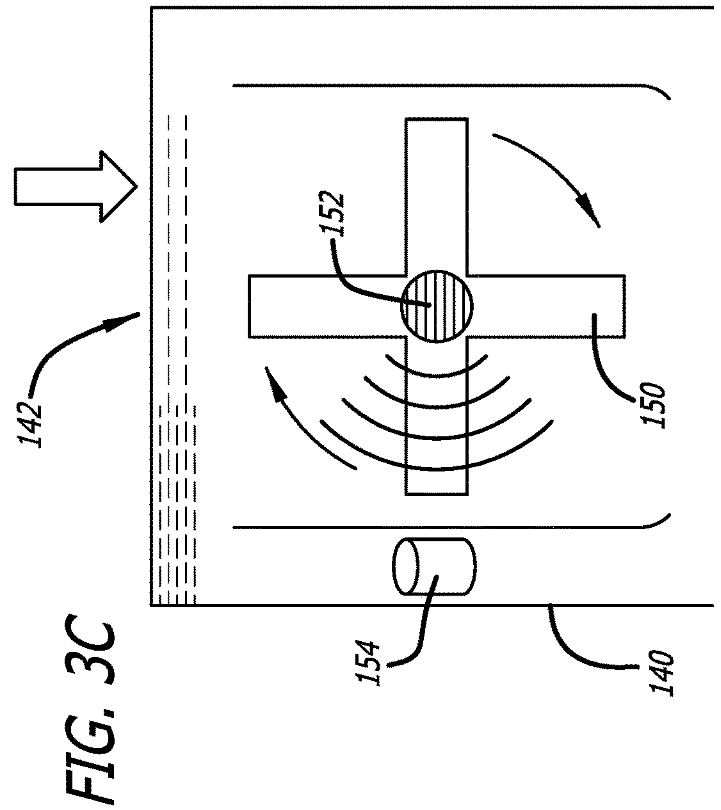
FIGS. 3B-3C illustrate a cross sectional view of an exemplary method of measuring the flow rate of a volume of fluid, in accordance with some embodiments.
Figure 3B:
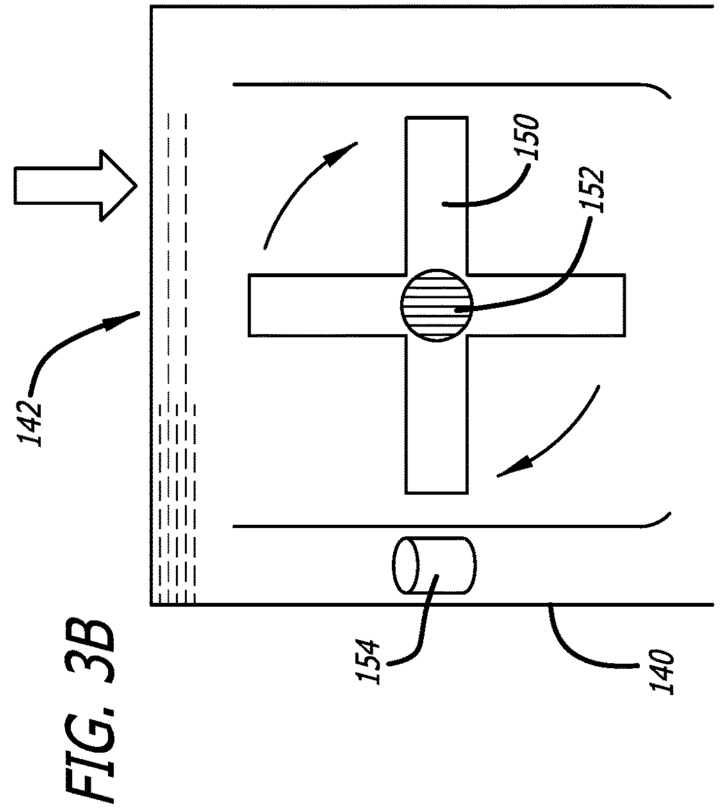

FIGS. 3B-3C illustrate cross sectional view of an exemplary method of measuring the flow rate of a volume of fluid, in accordance with some embodiments. In some embodiments, the receptacle 120 may receive therein a volume of fluid, which may be directed through the opening 128 of the receptacle 120 (see FIG. 1A) and into the proximal opening 142 of the flow meter 140. The volume of fluid may rotate the pinwheel 150 annularly within the lumen 146, as illustrated in FIG. 3B. The magnet 152 may be configured to rotate annularly with the pinwheel 150. The magnetic field generated by the magnet 152 may rotate, wherein the Hall-effect sensor 154 may be configured to detect the magnetic field rotation, as illustrated in FIG. 3C, as a plurality of high and low level square wave or pulses. The plurality of pulses may be configured to be transmitted to the console 160 to be converted into a flow rate value as described above.

Figure 3D:
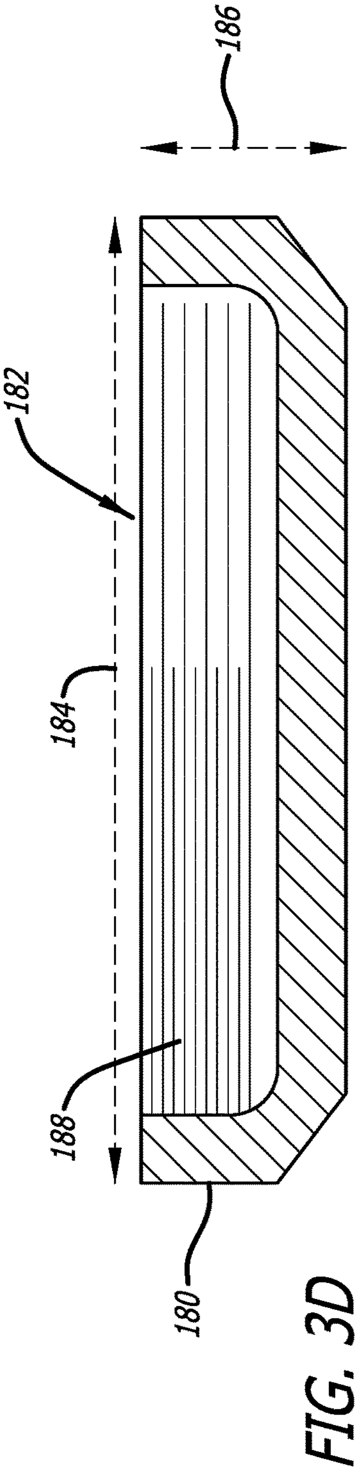
FIG. 3D illustrates a cross sectional view of the cap, in accordance with some embodiments.

FIG. 3D illustrates a cross sectional view of the cap 180, in accordance with some embodiments. In some embodiments, the cap 180 may have a proximal opening 182 configured to couple to the mating portion 132 of the receptacle 120. In some embodiments, the cap 180 may be couple to the mating portion 132 of the receptacle 120 in a twist fit, snap fit, press fit, interference fit, or the like. In some embodiments, the cap 180 may include a cap length 184 and a cap height 186. In some embodiments, the cap 180 may include threads 188 configured to couple with the threads of the mating portion 132 of the receptacle 120. In some embodiments, the threads 188 may include internal threads or an external threads. In some embodiments, the cap 180 may include the internal threads 188 configured to couple the cap 180 to the mating portion 132 of the receptacle 120. In some embodiments, the cap 180 may be detachably coupled to the mating portion 132 of the receptacle 120. In some embodiments, the cap 180 may be formed from polyethylene, polypropylene or the like. In some embodiments, the cap 180 may be 3D printed, extruded, injection molded, or the like.

Figure 4A:
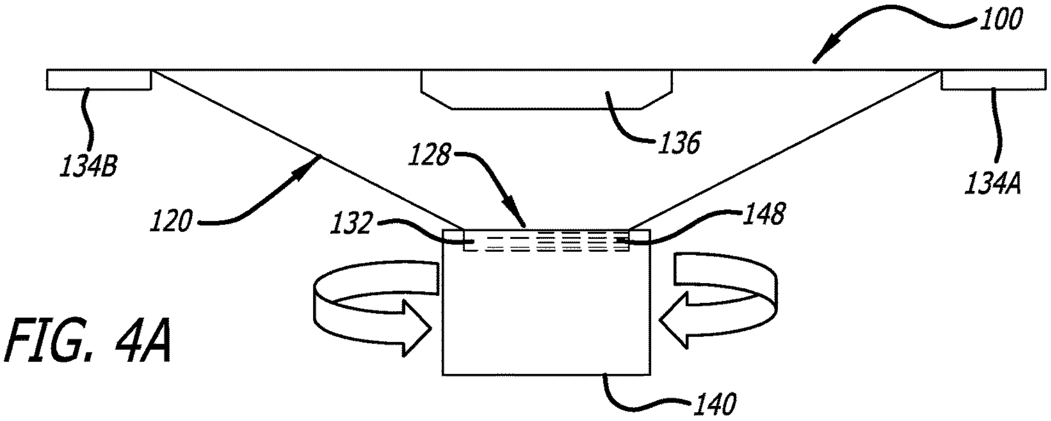
FIGS. 4A-4C illustrates a cross sectional view of an exemplary method of measuring urinary flow using the non-invasive urine output monitoring system, in accordance with some embodiments.
Figure 4B:
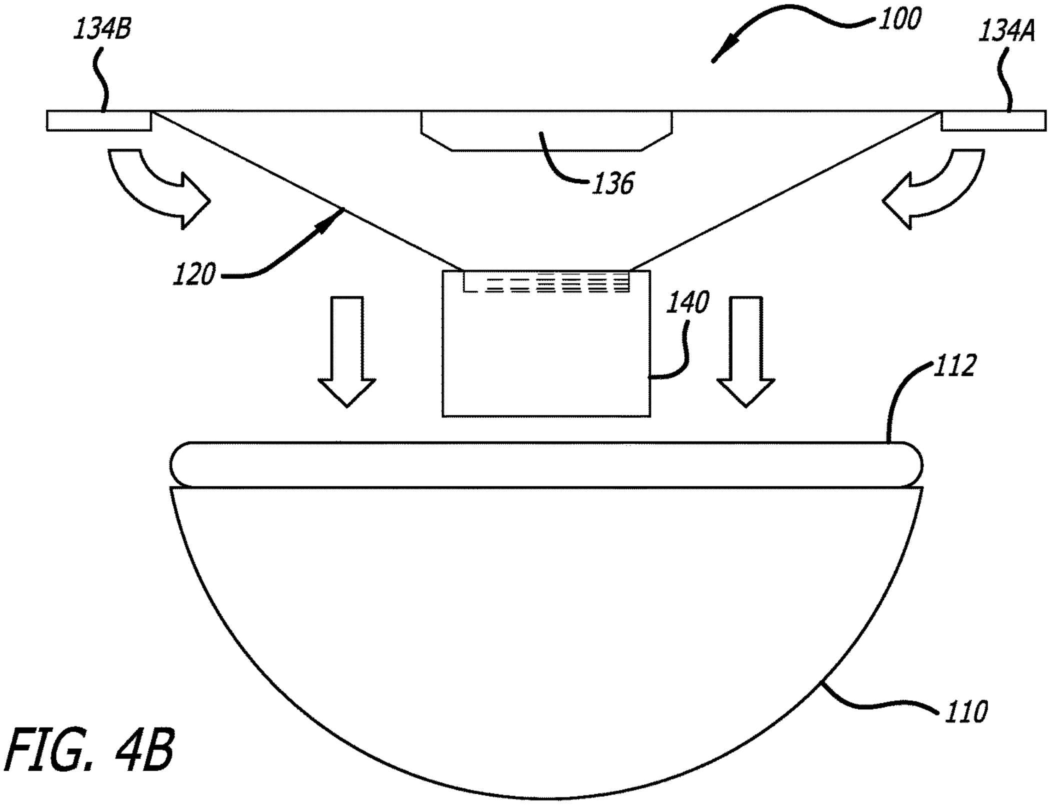
Figure 4C:
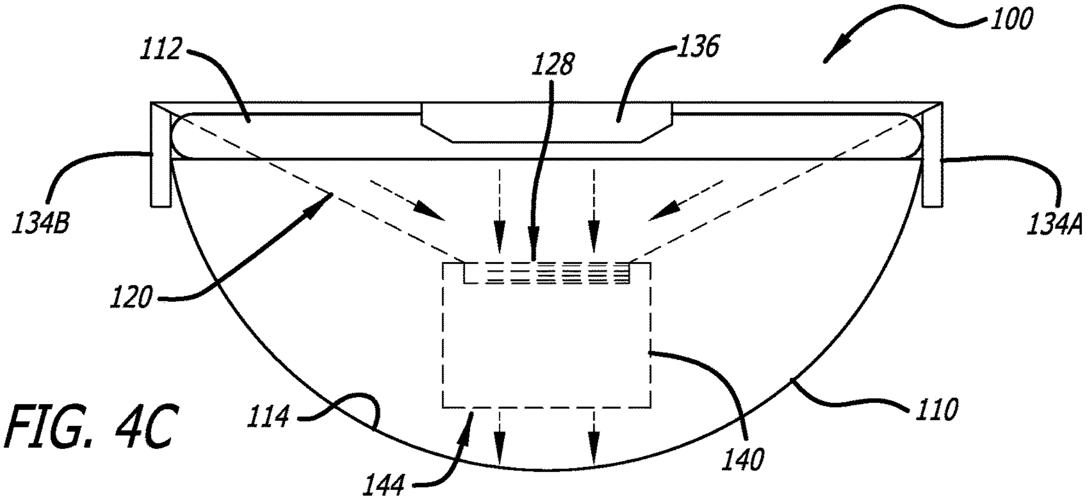

FIGS. 4A-4C illustrates a cross sectional view of an exemplary method of measuring urinary flow using the non-invasive urine output monitoring system 100, in accordance with some embodiments. As illustrated in FIG. 4A, in some embodiments, the non-invasive urine output monitoring system 100 including the receptacle 120 and flow meter 140 may be configured to measure urinary flow. In some embodiments, the receptacle 120 may be configured for measuring urinary flow by coupling the flow meter 140 to the mating portion 132 of the receptacle 120. In some embodiments, the threaded portion 148 of the flow meter 140 may be coupled to the mating portion 132 of the receptacle 120 in a twist fit. In some embodiments, the receptacle 120 may include right lateral flap 134A, the left lateral flap 134B, and the rigid front flap 136, each extending from the proximal portion of the receptacle 120.

Once the flow meter 140 is coupled to the receptacle 120, the receptacle 120 may be coupled to the toilet 110, as illustrated in FIG. 4B. The receptacle 120 may be coupled to the seat 112 of the toilet 110. The rigid front flap 136 and the two lateral flaps 134 may be used to couple the receptacle 120 to the seat 112. The two lateral flaps 134A/134B may be folded downward to further couple the receptacle 120 to the seat 112. Once the receptacle 120 is coupled to the seat 112, the receptacle 120 is configured to acquire a volume of fluid therein as illustrated in FIG. 4C. As the volume of fluid is acquired within the receptacle 120, the volume of fluid may pass from the opening 128 of the receptacle 120 through the flow meter 140. As the volume of fluid passes through the flow meter 140, the flow meter 140 may be configured to measure the rate of fluid flow through the flow meter 140. Once the volume of fluid passes through the flow meter 140, the volume of fluid may exit the distal opening 144 of the flow meter 140 into the bowl 114 of the toilet 110 for disposal. The receptacle 120 may then be detached from the toilet 110 and the flow meter 140 detached from the mating portion 132. The receptacle 120 may be disposed and the flow meter 140 may be coupled to a new receptacle 120 and configured to measure and analyze a new volume of fluid.

Figure 5A:
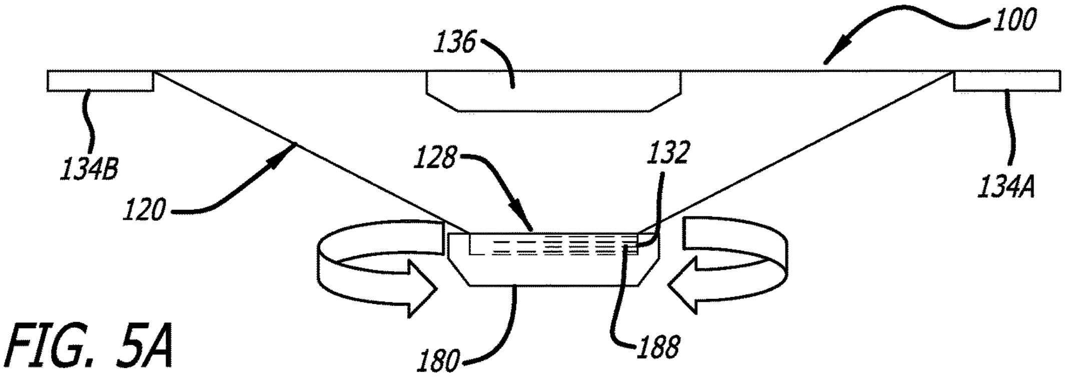
FIGS. 5A-5C illustrates a cross sectional view of an exemplary method of measuring and capturing urinary output using the non-invasive urine output monitoring system, in accordance with some embodiments.
Figure 5B:
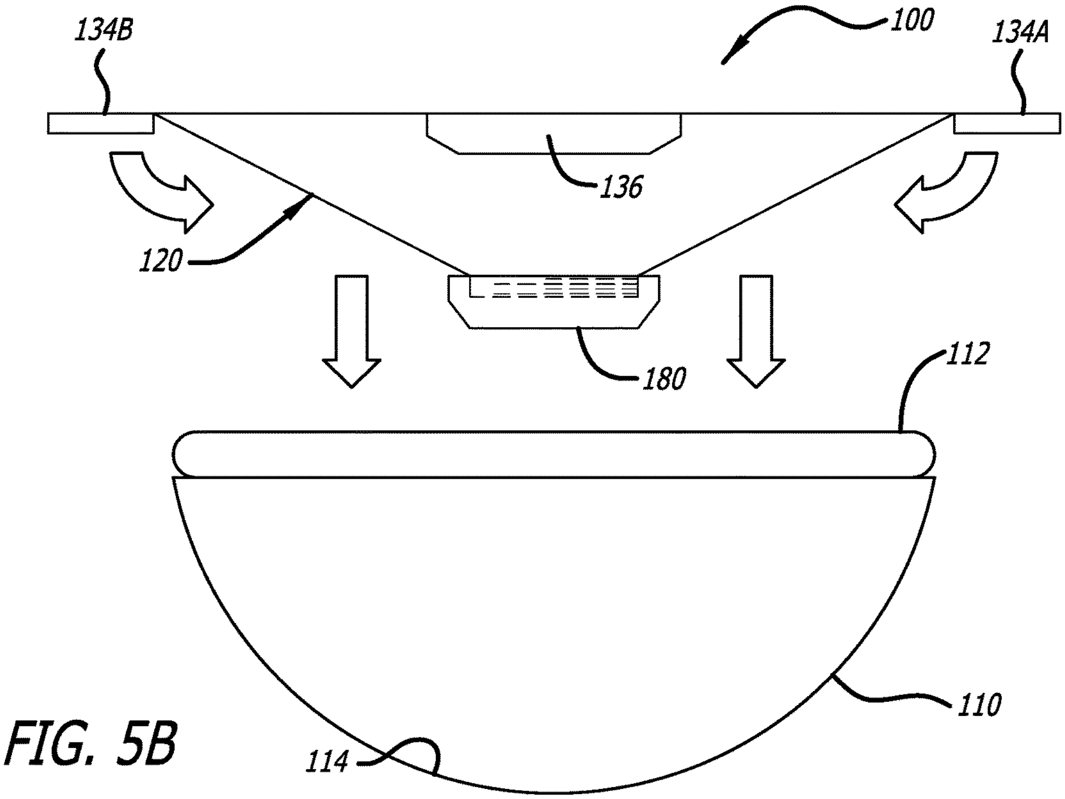
Figure 5C:
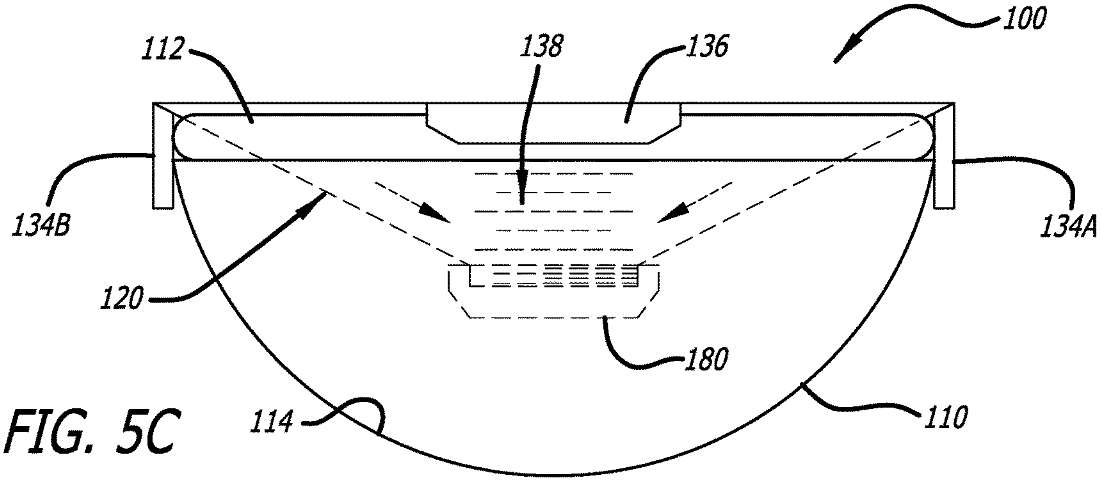

FIGS. 5A-5C illustrates a cross sectional view of an exemplary method of measuring and capturing urinary output using the non-invasive urine output monitoring system 100, in accordance with some embodiments. As illustrates in FIG. 5A, in some embodiments, the non-invasive urine output monitoring system 100 including the receptacle 120 that may be configured for capturing and measuring a volume of fluid therein by coupling the cap 180 to the mating portion 132 of the receptacle 120. The cap 180 may be coupled to the mating portion 132 by coupling the threads 188 of the cap 180 to the threads of the mating portion 132 through a press fit, snap fit, interference fit, twist fit or the like.

Once the cap 180 is coupled to the mating portion 132 of the receptacle 120, as illustrated in FIG. 5B, the receptacle 120 may be configured to be coupled to the toilet 110. In some embodiments, the receptacle 120 may be coupled to the seat 112 of the toilet 110. The receptacle 120 may be coupled to the seat 112 by the rigid front flap 136 and the two or more lateral flaps 134A/134B. The rigid front flap 136 and the right lateral flap 134A and the left lateral flap 134B may be coupled to the seat 112 by being folded downward to further couple the receptacle 120 to the seat 112. The receptacle 120 may be coupled to the seat 112 in a way that the receptacle 120 may be suspended within the bowl 114 of the toilet 110. Once the receptacle 120 is coupled to the seat 112 as illustrated in FIG. 5C, the receptacle 120 may be configured to capture a volume of fluid therein. The volume of fluid may be measured using the plurality of volume markers 138 within the receptacle 120. The captured volume of fluid may then be collected for further analysis by uncoupling the receptacle 120 from the toilet 110 with the volume of fluid therein.

Figure 6:
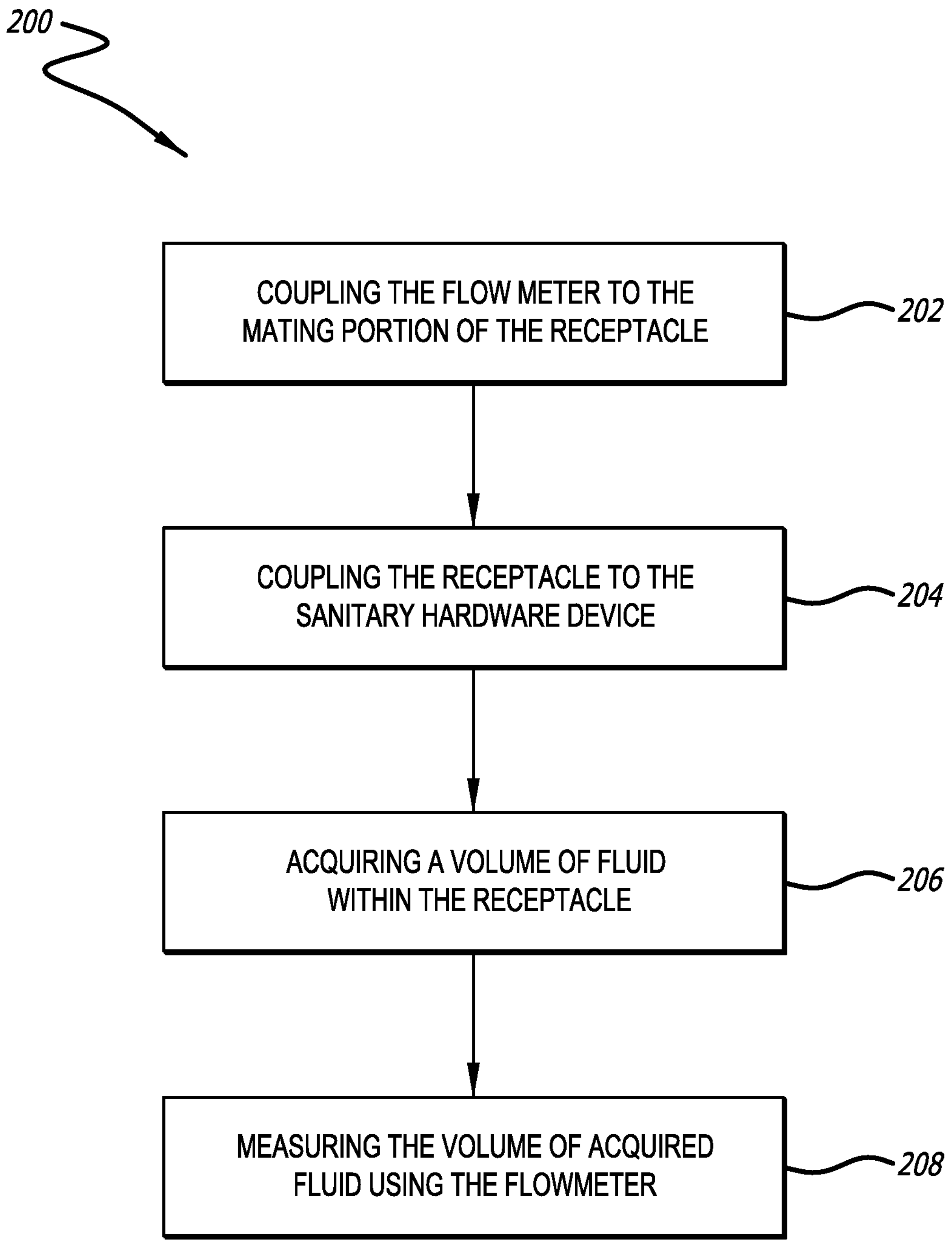
FIG. 6 illustrates a flow chart of an exemplary method of measuring urinary flow using the non-invasive urine output monitoring system, in accordance with some embodiments.

FIG. 6 illustrates a flow chart of an exemplary method 200 of measuring urinary flow using the non-invasive urinary output monitoring system 100, in accordance with some embodiments. In some embodiments, the method 200 of measuring urinary flow includes coupling the flow meter 140 to the mating portion 132 of the receptacle 120 (block 202). In some embodiments, coupling includes detachably coupling the threaded portion 148 of the flow meter 140 to the mating portion 132 of the receptacle 120 in a press fit, a snap fit, an interference fit, a twist fit or the like. In some embodiments, coupling includes confirming the flow meter 140 is wirelessly coupled to a computing device. In some embodiments, coupling includes confirming the flow meter 140 is configured to acquire flow data.

The method 200 further includes coupling the receptacle 120 to the sanitary hardware device 110 (block 204). In some embodiments, coupling the receptacle to the sanitary hardware device 110 includes coupling the receptacle to a seat 112 of the sanitary hardware device 110 in that the receptacle body 122 is suspended within a bowl 114 of the sanitary hardware device 110. In some embodiments, coupling includes detachably securing the rigid front flap 136 to the front of the sanitary hardware device 110. In some embodiments, coupling includes folding the two or more lateral flaps 134 downward, each along a score line, to further couple the receptacle 120 to the seat 112. The method 200 further includes acquiring a volume of fluid within the receptacle 120 (block 206). In some embodiments, acquiring includes a user disposing of a volume of urine within the receptacle 120. The method 200 further includes measuring the volume of acquired fluid using the flow meter 140 (block 208). In some embodiments, measuring includes passing the volume of fluid through the flow meter 140 to measure the urinary flow. In some embodiments, measuring includes transmitting a measured urinary flow data to the computing device.

Figure 7:
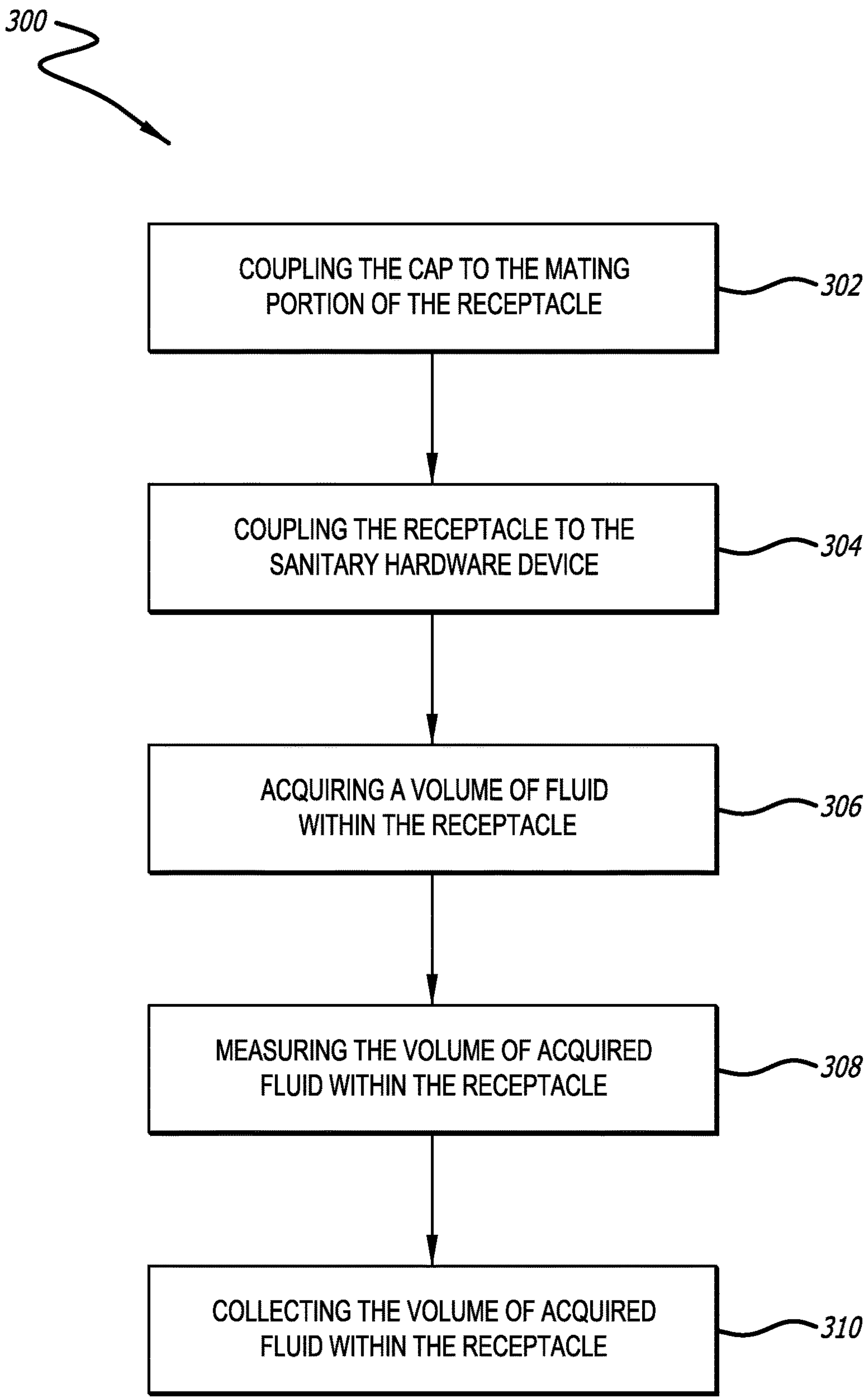
FIG. 7 illustrates a flow chart of an exemplary method of measuring and capturing urine output using the non-invasive urine output monitoring system, in accordance with some embodiments.

FIG. 7 illustrates a flow chart of the exemplary method 300 of measuring and capturing a volume of urine output using the non-invasive urinary output monitoring system 100, in accordance with some embodiments. In some embodiments, the method 300 of measuring and capturing a volume of urine output includes coupling the cap 180 to the mating portion 132 of the receptacle 120 (block 302). In some embodiments, coupling includes coupling the threaded portion 188 of the cap 180 to the mating portion 132 of the receptacle 120 in a press fit, a snap fit, an interference fit, a twist fit or the like. The method 300 further includes coupling the receptacle 120 to the sanitary hardware device 110 (block 304), as described above. The method 200 further includes acquiring a volume of fluid within the receptacle 120 (block 306), as described above. The method 300 further includes measuring the volume of acquired fluid within the receptacle 120 (block 308). In some embodiments, measuring includes visually determining the volume of acquired fluid using the plurality of measurement markings within the receptacle 120. In some embodiments, the method 300 further includes collecting the volume of acquired fluid within the receptacle 120 (block 310). In some embodiments, collecting includes collecting a portion of the volume of acquired fluid or collecting the entire volume of acquired fluid for further analysis.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A urinary output monitoring system configured to measure urinary flow or collect and measure a volume of urine, comprising:
- a receptacle having a receptacle body configured to receive urine therein, the receptacle body having a plurality of volume markings for measuring the volume of urine when the urine is collected in the receptacle;
- a proximal portion of the receptacle including two lateral flaps and one front rigid flap, each flap extending from the proximal portion and configured to secure the receptacle to a sanitary hardware device to prevent movement when engaged by a user; and
- a distal portion of the receptacle including an opening and a threaded mating portion extending from the distal portion, the threaded mating portion configured to detachably couple a threaded portion of a reusable flow meter in a twist or screw fit for measuring a flow rate of the volume of urine through the receptacle.

2. The urinary output monitoring system according to claim 1, wherein the reusable flow meter includes a pinwheel flow meter having a proximal end including a proximal opening, a distal end including a distal opening, and a lumen therethrough; the proximal end of the pinwheel flow meter has the threaded portion configured to detachably couple to the threaded mating portion of the receptacle; and the pinwheel flow meter has a pinwheel therein and a magnet thereon for detection by a Hall-effect sensor of the pinwheel flow meter.

3. The urinary output monitoring system according to claim 2, wherein the Hall-effect sensor is in wireless communication with a console, or wired to the console, the console including a processor, an energy source, and a non-transitory computer-readable medium having stored thereon a plurality of logic modules for determining the flow rate of the volume of urine passing through the pinwheel flow meter.

4. The urinary output monitoring system according to claim 3, wherein the plurality of logic modules, when executed by the processor, are configured to perform operations including:
- activating the Hall-effect sensor;
- detecting and acquiring a plurality of pulses from the magnet over a unit of time;
- associating the plurality of pulses with rate-of-flow values;

associating the rate-of-flow values with time-of-day values in pairings of the rate-of-flow values and the time-of-day values;

storing the pairings of the rate-of-flow values and the time-of-day values; and transmitting the pairings of the rate-of-flow values and the time-of-day values to a computing device.

5. The urinary output monitoring system according to claim 3, wherein the console is in wireless communication with a computing device.

6. The urinary output monitoring system according to claim 2, wherein the threaded portion of the pinwheel flow meter includes an external threaded portion.

7. The urinary output monitoring system according to claim 2, wherein the threaded portion of the pinwheel flow meter includes an internal threaded portion.

8. The urinary output monitoring system according to claim 1, wherein the threaded mating portion is further configured to detachably couple a cap for collecting the volume of urine within the receptacle for measuring the volume of urine by way of the plurality of volume markings.

9. The urinary output monitoring system according to claim 1, wherein the receptacle body includes an inverse truncated elliptical cone.

10. The urinary output monitoring system according to claim 9, wherein each flap of the two lateral flaps includes a score line configured to allow each flap to fold downward to couple with the sanitary hardware device.

11. The urinary output monitoring system according to claim 10, wherein the sanitary hardware device includes a toilet.

12. The urinary output monitoring system according to claim 1, wherein the threaded mating portion of the receptacle includes internal threads.

13. The urinary output monitoring system according to claim 1, wherein the threaded mating portion of the receptacle includes external threads.

14. A method of using a urinary output monitoring system, comprising:

coupling a threaded portion of a reusable flow meter to a threaded mating portion extending from a distal portion of a receptacle of the urinary output monitoring system in a twist or screw fit;

coupling a proximal portion of the receptacle to a sanitary hardware device, the proximal portion including two lateral flaps and one front rigid flap, each flap extending from the proximal portion and configured to secure the receptacle to the sanitary hardware device to prevent movement when engaged by a user;

receiving a volume of urine within a receptacle body of the receptacle, the receptacle body having a plurality of volume markings for measuring the volume of urine collected in the receptacle; and measuring a flow rate of the volume of urine through the receptacle using the reusable flow meter.

15. The method according to claim 14, wherein the front rigid flap extends from the proximal portion, the distal portion has an opening in the threaded mating portion extending therefrom, and the threaded mating portion is configured to detachably couple the reusable flow meter thereon in the twist or screw fit.

16. The method according to claim 15, wherein the reusable flow meter includes a pinwheel flow meter having a proximal end including a proximal opening, a distal end including a distal opening, and a lumen therethrough; the proximal end of the pinwheel flow meter has a threaded portion configured to detachably couple to the threaded mating portion of the receptacle; and the pinwheel flow meter has a pinwheel therein and a magnet thereon for detection by a Hall-effect sensor in communication with a console including a processor, an energy source, and non-transitory computer-readable medium having stored thereon a plurality of logic modules for determining the flow rate of the volume of urine passing through the pinwheel flow meter.

17. The method according to claim 13, wherein coupling the receptacle to the sanitary hardware device includes folding each flap of the two lateral flaps downward along a score line to couple each lateral flap to a side of the sanitary hardware device.

* * * * *